US00PP37125P2

(12) United States Plant Patent
Okusada et al.

(10) Patent No.: US PP37,125 P2
(45) Date of Patent: Dec. 9, 2025

(54) MANDARIN PLANT NAMED 'MIKANKEN14'

(50) Latin Name: ***Citrus* sp.**
Varietal Denomination: Mikanken14

(71) Applicant: EHIME PREFECTURE, Ehime (JP)

(72) Inventors: Takehiro Okusada, Ehime (JP); Mitsutoshi Okamoto, Ehime (JP); Yukinori Shigematsu, Ehime (JP); Taizo Ninomiya, Ehime (JP); Yoji Hyodo, Ehime (JP); Hiromichi Yakushiji, Ehime (JP); Takae Sakimoto, Ehime (JP); Saki Miyoshi, Ehime (JP); Saki Yamamoto, Ehime (JP); Toya Hioki, Ehime (JP); Yasuyuki Masamoto, Ehime (JP); Kei Kinoshita, Ehime (JP); Haruhito Nakata, Ehime (JP); Takehiro Kikuchi, Ehime (JP); Daijiro Sugawara, Ehime (JP); Hiroaki Mido, Ehime (JP)

(73) Assignee: EHIME PREFECTURE, Matsuyama (JP)

( * ) Notice: Subject to any disclaimer, the term of this patent is extended or adjusted under 35 U.S.C. 154(b) by 0 days.

(21) Appl. No.: 19/182,941

(22) Filed: Apr. 18, 2025

(51) Int. Cl.
*A01H 5/08* (2018.01)

(52) U.S. Cl.
USPC ..... Plt./202

(58) Field of Classification Search
USPC ..... Plt./202
CPC ..... A01H 6/785; A01H 5/08
See application file for complete search history.

*Primary Examiner* — Keith O. Robinson
(74) *Attorney, Agent, or Firm* — Seckel IP, PLLC

(57) ABSTRACT

A new variety of *Citrus* sp. plant named 'Mikanken14' that has vivid orange as the surface predominant color of the fruit, strong orange as main color of the flesh, and very early to early maturity of the fruit for consumption.

3 Drawing Sheets

Common name: Mandarin.
Botanical classification: *Citrus* sp.
Variety denomination: 'Mikanken14'.

BACKGROUND OF THE NEW VARIETY

The present invention relates to a new and distinct variety of mandarin, *Citrus* sp., which has been given the variety denomination 'Mikanken14'.

ORIGIN OF THE VARIETY

The parent varieties are 'Unknown mandarin variety' (male parent) and 'Mikanken4' (female parent) (U.S. Plant patent application Ser. No. 18/944,163), respectively.

The variety was developed and propagated in Uwajima, Ehime, Japan.

The variety was reproduced asexually by vegetative reproduction by top grafting one-year-old scions on rootstocks, in Uwajima, Ehime, Japan. The name of the rootstock is 'MIYAGAWAWASE' (not patented).

In 2005, crossing the parent varieties and collecting seeds to be grown in the next year.

In 2006 and 2007, seeds were planted and grown.

In 2008, scions were grafted on top of root stock.

In 2010, the first fruit was harvested, and lines were primarily selected.

In 2012, lines were secondary selected.

In 2024, breeding was completed with DUS status confirmed (distinct, uniform, and stable), whereby it was confirmed that the instant tree reproduces true to type in successive generations of asexual reproduction, and the variety was named 'Mikanken14'.

Cultivation of variety does not require special conditions or treatments. The variety is currently mainly intended for fruit production.

SUMMARY OF THE VARIETY

This new mandarin plant 'Mikanken14' has medium orange as the surface predominant color of the fruit, medium orange as main color of the flesh, and very early to early maturity of the fruit for consumption, that distinguish it notably from its female parent 'Mikanken4' (dark orange surface as predominant color of the fruit, dark orange as main color of the flesh, late maturity of the fruit for consumption)

Also, 'Mikanken14' has very thin rind thickness of the fruit, absent or very sparse of filling of the core, very small diameter of the core, that distinguish it notably from its comparative variety 'HAREHIME' (not patented in the U.S., plant variety protection granted in Japan) (thin rind thickness of the fruit, sparse of filling of the core, medium diameter of the core).

In addition, the fruit of 'Mikannken14' has the following characteristics: the fruit size is from 150 g to 200 g, the strength of the segment walls is weak, the fruit has no seeds, in early December, the total soluble solids (Brix) of juice are about 15 degrees and the juice acidity is medium, and the time of maturity of the fruit is from late December to January.

Table 1 shows a comparison between the instant variety 'Mikanken14' and Female parent variety 'Mikanken4', as follows (average evaluation):

TABLE 1

Comparison between 'Mikanken14' and 'Mikanken4'

| Characteristics | Female parent variety 'Mikanken4' States | Present variety 'Mikanken14' States |
|---|---|---|
| Fruit: surface predominant color | Dark orange | Vivid orange |
| Fruit: main color of flesh | Dark orange | Strong orange |
| Plant: time of maturity of fruit for consumption | Late | Very early to early |

Table 2 shows a comparison between the instant variety 'Mikanken14' and comparative variety 'HAREHIME'

TABLE 2

Comparison between 'Mikanken14' and 'HAREHIME'

| Characteristics | Comparative variety 'HAREHIME' States | Present variety 'Mikanken14' States |
|---|---|---|
| Fruit: rind thickness | Thin | Very thin |
| Fruit: filling of core | Sparse | Absent or very sparse |
| Fruit: diameter of core | Medium | Very small |

BRIEF DESCRIPTION OF THE DRAWINGS

In the accompanying drawings, which are as nearly true as is reasonable possible to make in a color illustration of this type.

Figure 1:
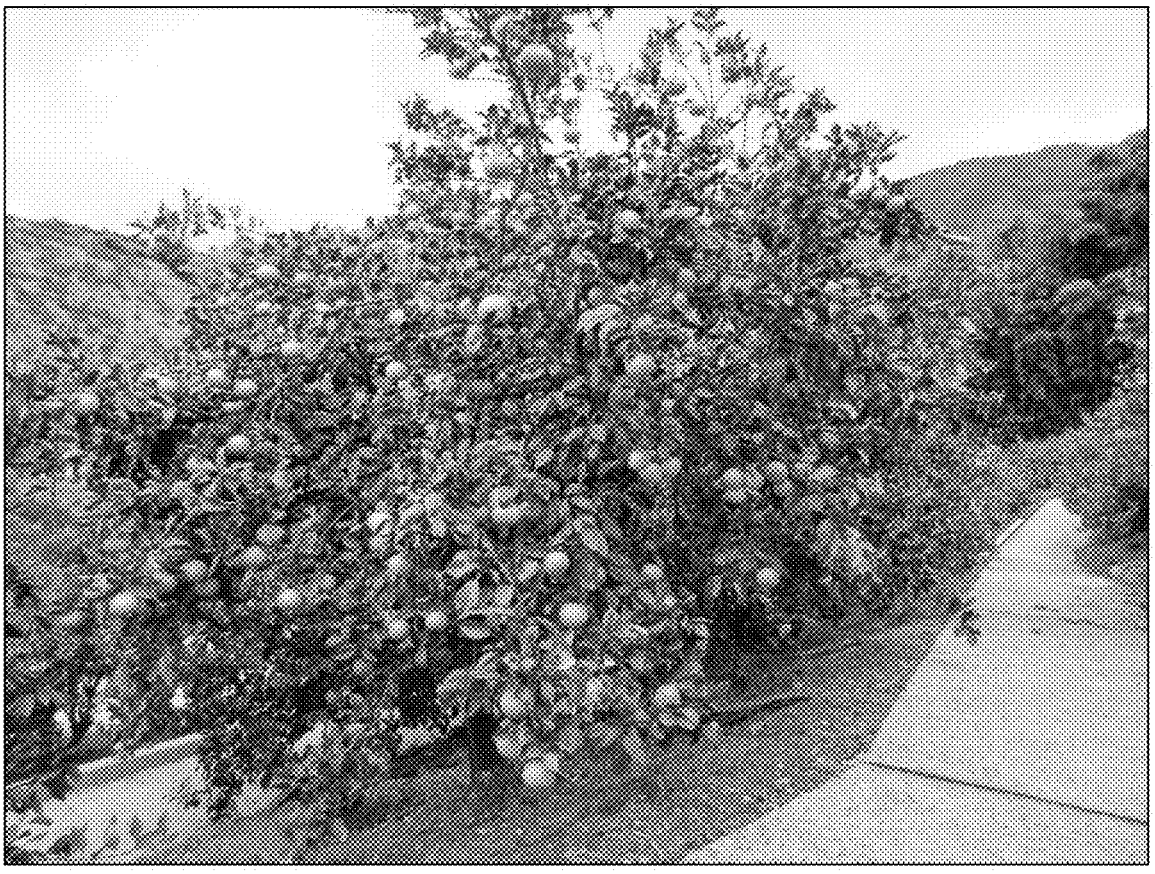
FIG. 1 is a color photograph showing a general view of an illustrative 12-year old mandarin tree of the variety named 'Mikanken14' bearing fruits.
Figure 2:
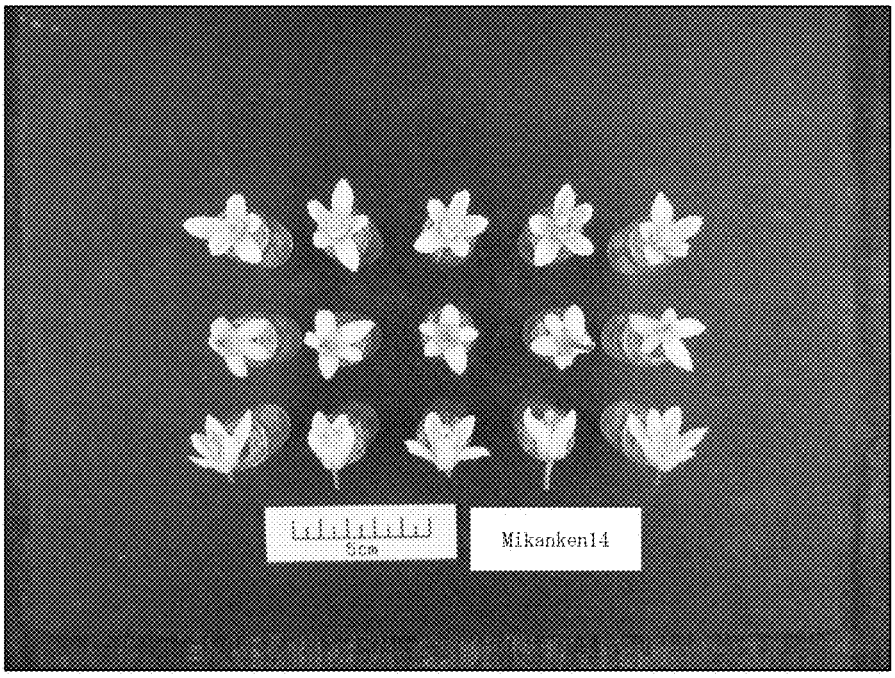
FIG. 2 is a color photograph showing flowers of 'Mikanken14'.
Figure 3:
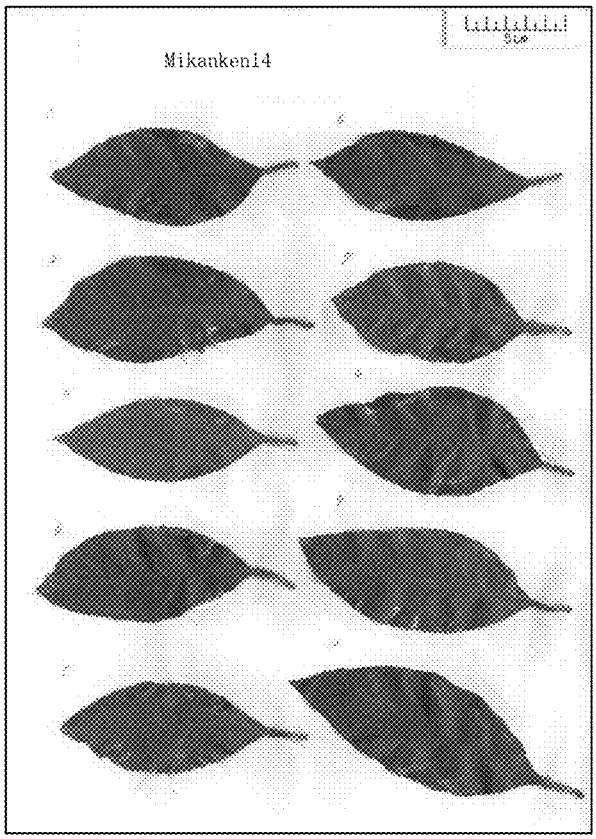
FIG. 3 is a color photograph showing leaves of 'Mikanken14'.
Figure 4:
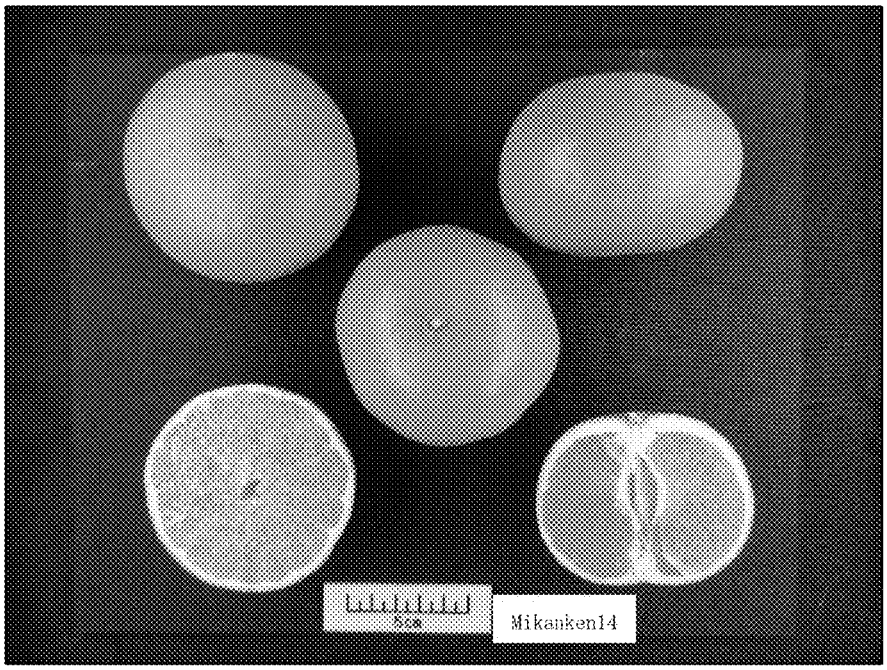
FIG. 4 is a color photograph showing fruits of 'Mikanken14'.
Figure 5:
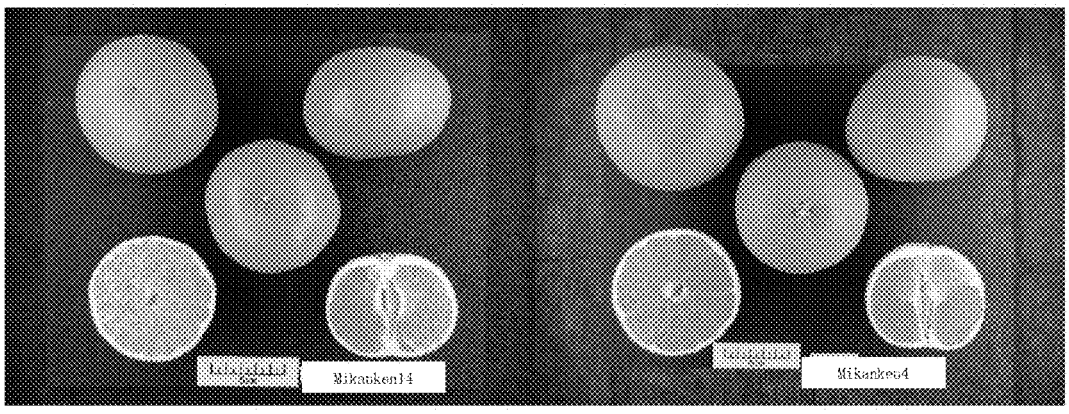
FIG. 5 is a color photograph showing fruits of 'Mikanken14' and 'Mikanken4', which indicates the difference of fruit: surface predominant color and main color of the flesh.
Figure 6:
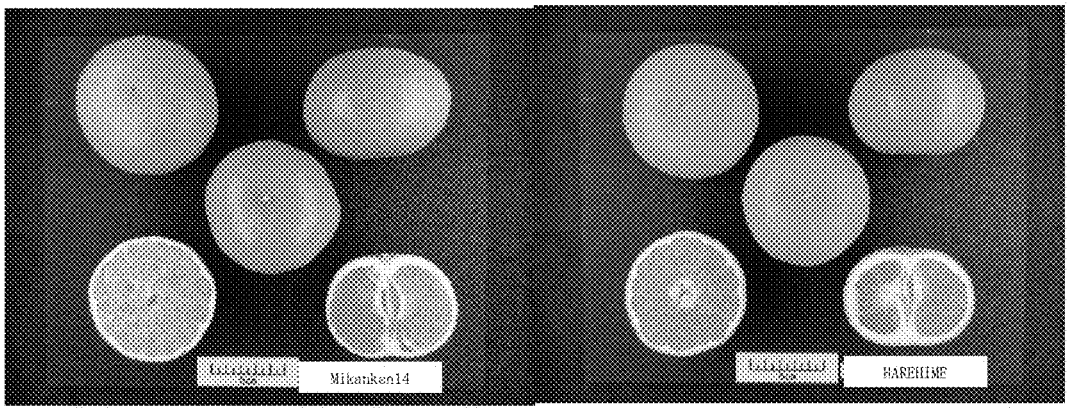
FIG. 6 is a color photograph showing fruits of 'Mikanken14' and 'HAREHIME', which indicates the difference of the fruit: thickness of rind, filling of the core, diameter of the core.

Due to chemical and/or digital development, processing and printing, the plants or portions of plants depicted in the photographs may or may not be precisely accurate when compared to the actual botanical specimens.

DETAILED DESCRIPTION OF THE INVENTION

Table 3 shows the botanical description of the 'Mikanken14' plants evaluated in 2023 (including the comparison with the reference plants 'Mikanken4' and 'HAREHIME'). The values as provided are average. The ages of the trees evaluated was 13 years after grafted on top of Rootstock, and the location of the trees evaluated was in Uwajima, Ehime, Japan.

Colors are given according to the J.H.S. (Japan Horticultural Society) Color Chart (second edition, 1997 reprint).

BOTANICAL DESCRIPTION

TABLE 3

Botanical description of 'Mikanken 14'

| Characteristics | States | Values |
|---|---|---|
| Ploidy | Diploid | |
| Tree: growth habit | Spreading | |
| Tree: density of spines | Absent or sparse | |
| Tree: height | | 2.5 m |
| Tree: spread | | 3.0 m |
| Tree: trunk diameter (10 cm above the grafted area) | | 32.5 cm |
| Tree: trunk texture | Rough | |
| Tree: crotch angle | | 71° |
| Branch: length | | 11.5 cm |
| Branch: diameter | | 3.8 cm |
| Branch: texture | Smooth | |
| Length of spines | | 4.7 cm |
| Leaf blade: length (apical leaflet in case of compound leaf) | Long | 11.4 cm |
| Leaf blade: width (apical leaflet in case of compound leaf) | Broad | 5.1 cm |
| Leaf blade: ratio length/width (apical leaflet in case of compound leaf) | Small | 2.2 |
| Leaf blade: shape in cross section (apical leaflet in case of compound leaf) | Intermediate | |
| Leaf blade: twisting | Absent or weak | |
| Leaf blade: blistering | Absent or weak | |
| Leaf blade: color | Dark green | 3509 (JHS Color Chart) |
| Leaf blade: undulation of margin | Intermediate | |
| Leaf blade: incisions of margin | Absent | |
| Leaf blade: shape of apex | Acute | |
| Leaf blade: emargination at tip | Absent | |
| Petiole: length | Medium | 1.9 cm |
| Petiole: presence of wings | Present | |
| Varieties with petiole wings present only: petiole: width of wings | Narrow | 4.1 mm |
| Flower: diameter of calyx | | 0.8 cm |
| Flower: length of petal | Short | 13.4 mm |
| Flower: width of petal | Broad | 6.2 mm |
| Flower: ratio length/width of petal | | 2.2 |
| Flower: length of stamens | | 9.8 mm |
| Anther: color | Pale reddish yellow | 2202 JHS Color Chart |
| Style: length | | 7.0 mm |
| Infructescence: clustering of fruits | Absent | |
| Fruit: length | | 5.6 cm |
| Fruit: diameter | | 7.1 cm |
| Fruit: ratio length/diameter | | 1.27 |
| Fruit: position of broadest part | At middle | |
| Fruit: shape in transverse section | Circular | |
| Fruit: general shape of proximal part (excluding neck, collar and depression at stalk end) | Flattened | |
| Fruit: presence of neck | Absent | |
| Fruit: presence of depression at stalk end | Absent | |
| Fruit: presence of constriction at stalk end | Absent | |
| Fruit: number of radial grooves at stalk end | Absent or few | 0 |
| Fruit: presence of collar | Absent | |
| Fruit: abscission layer between floral disc and fruit | Absent or weakly developed | |
| Fruit: general shape of distal part (excluding nipple, bulging of navel and depression at distal end) | Flattened | |
| Fruit: presence of depression at distal end | Present | |

TABLE 3-continued

Botanical description of 'Mikanken 14'

| Characteristics | States | Values |
|---|---|---|
| Fruit: depth of depression at distal end | | 1.3 mm |
| Fruit: diameter of depression at distal end | | 9.0 mm |
| Fruit: presence of areola | Incomplete | |
| Fruit: type of areola | Smooth | |
| Fruit: diameter of areola | | 0.9 cm |
| Fruit: diameter of stylar scar | | 1.4 mm |
| Fruit: persistence of style | None | |
| Fruit: presence of navel opening | Absent | |
| Fruit: presence of radial grooves at distal end | Absent | |
| Fruit: surface: predominant color(s) | Vivid orange | 1605 (JHS Color Chart) |
| Fruit surface: glossiness | Strong | |
| Fruit surface: roughness | Smooth | |
| Fruit surface: size of oil glands | All more or less the same size | |
| Fruit surface: size of larger oil glands | Medium | |
| Fruit surface: conspicuousness of larger oil glands | Strong | |
| Fruit surface: presence of pitting and pebbling on oil glands | Pitting and pebbling absent | |
| Fruit rind: thickness | Very thin | 1.5 mm |
| Fruit rind: adherence of flesh | Weak to medium | |
| Fruit rind: strength | Medium | |
| Fruit rind: oiliness | Dry | |
| Fruit rind: conspicuousness of oil glands on inner surface | Absent or weakly conspicuous | |
| Fruit: color of albedo | Yellowish white | 2502 (JHS Color Chart) |
| Fruit: density of albedo | Medium | |
| Fruit: amount of albedo adhering to flesh (strand excluded) | Medium | |
| Fruit: presence of albedo strands | Present | |
| Fruit: amount of albedo strands | Medium | |
| Fruit: main color of flesh | Strong orange | 1606 (JHS Color Chart) |

TABLE 3-continued

Botanical description of 'Mikanken 14'

| Characteristics | States | Values |
|---|---|---|
| Fruit: filling of core | Absent of very sparse | |
| Fruit: diameter of core | Very small | 9.4 mm |
| Fruit: presence of rudimentary Segments | Absent or very weak | |
| Fruit: number of well-developed segments | | 11 |
| Fruit: coherence of adjacent segment walls | Medium | |
| Fruit: strength of segment wails | Weak | |
| Fruit: length of juice vesicles | | 4.8 mm |
| Fruit: thickness of juice vesicles | | 2.9 mm |
| Fruit conspicuousness of juice vesicle walls | High | |
| Fruit; coherence of juice vesicles | Medium | |
| Fruit: presence of navel (viewed internally) | Absent or very rare | |
| Fruit: juiciness | High | |
| Fruit juice: total soluble solids | High | 14.2 (Brix) |
| Fruit juice: acidity | Medium | 1.07 |
| Fruit: strength of fiber | Weak | |
| Fruit: number of seeds (open pollinated) | Absent or very few | 0 |
| Seed: polyembryony | Absent | |
| Plant: time of maturity of fruit for consumption | Very early to early | December |
| Plant: fruit: parthenocarpy | Present | |
| Fruit productivity | | 35 ton/ha |

Other features of the plant are as follows:

*Disease and pest resistance*.—Not observed to date.

*Tree Hardiness*.—USDA Hardiness Zone 9a-9b (until −3° C.).

The invention claimed is:

1. A new and distinct variety of *Citrus* sp. plant named 'Mikanken14', substantially as described and illustrated herein.

* * * * *